United States Patent [19]

Lundquist

[11] 3,965,897
[45] June 29, 1976

[54] MEASURED VOLUME DRUG ADMINISTRATION DEVICE FOR USE WITH INTRAVENOUS FEEDING PUMP

[75] Inventor: Ingemar H. Lundquist, Oakland, Calif.

[73] Assignee: Origo, Incorporated, Hayward, Calif.

[22] Filed: Oct. 11, 1974

[21] Appl. No.: 514,219

[52] U.S. Cl. ................... 128/214 R; 128/218 G; 128/220; 128/237; 128/278
[51] Int. Cl.² ................ A61M 5/14; A61M 5/315
[58] Field of Search ........ 128/214 R, 214 C, 214.2, 128/215, 218 R, 218 G, 218 P, 220, 234, 238, 276, 278

[56] References Cited
UNITED STATES PATENTS

| 1,410,530 | 3/1922 | Larche | 128/220 |
|---|---|---|---|
| 2,489,600 | 11/1949 | Tydings et al. | 128/218 M |
| 3,001,525 | 9/1961 | Hendricks | 128/214 C |
| 3,378,006 | 4/1968 | Burke | 128/214 R |

FOREIGN PATENTS OR APPLICATIONS

| 76,771 | 12/1954 | Netherlands | 128/218 G |
|---|---|---|---|
| 112,124 | 11/1918 | United Kingdom | 128/220 |

Primary Examiner—Dalton L. Truluck
Attorney, Agent, or Firm—Flehr, Hohbach, Test, Albritton & Herbert

[57] ABSTRACT

This invention provides a device for first mixing and then dispensing a measured volume of a drug diluted in a predetermined ratio with an intravenous feeding solution. The device is inserted between the supply container and an intravenous feeding pump. The device is contained in a transparent tube marked with indicia showing volumes therein. A close-fitting piston, preferably made of soft rubber, fits within the container and is movable therein. A rigid stem extends axially through the piston and out of the chamber and is of sufficient strength so that it can be grasped by hand for manually moving the piston within the chamber. This conduit provides a throughflow passage from the inlet to the outlet, and thence to the intravenous feeding pump. A flexible germ barrier is provided for sealing the interior wall of the container from contamination by air at all times it is in the flow system.

6 Claims, 2 Drawing Figures

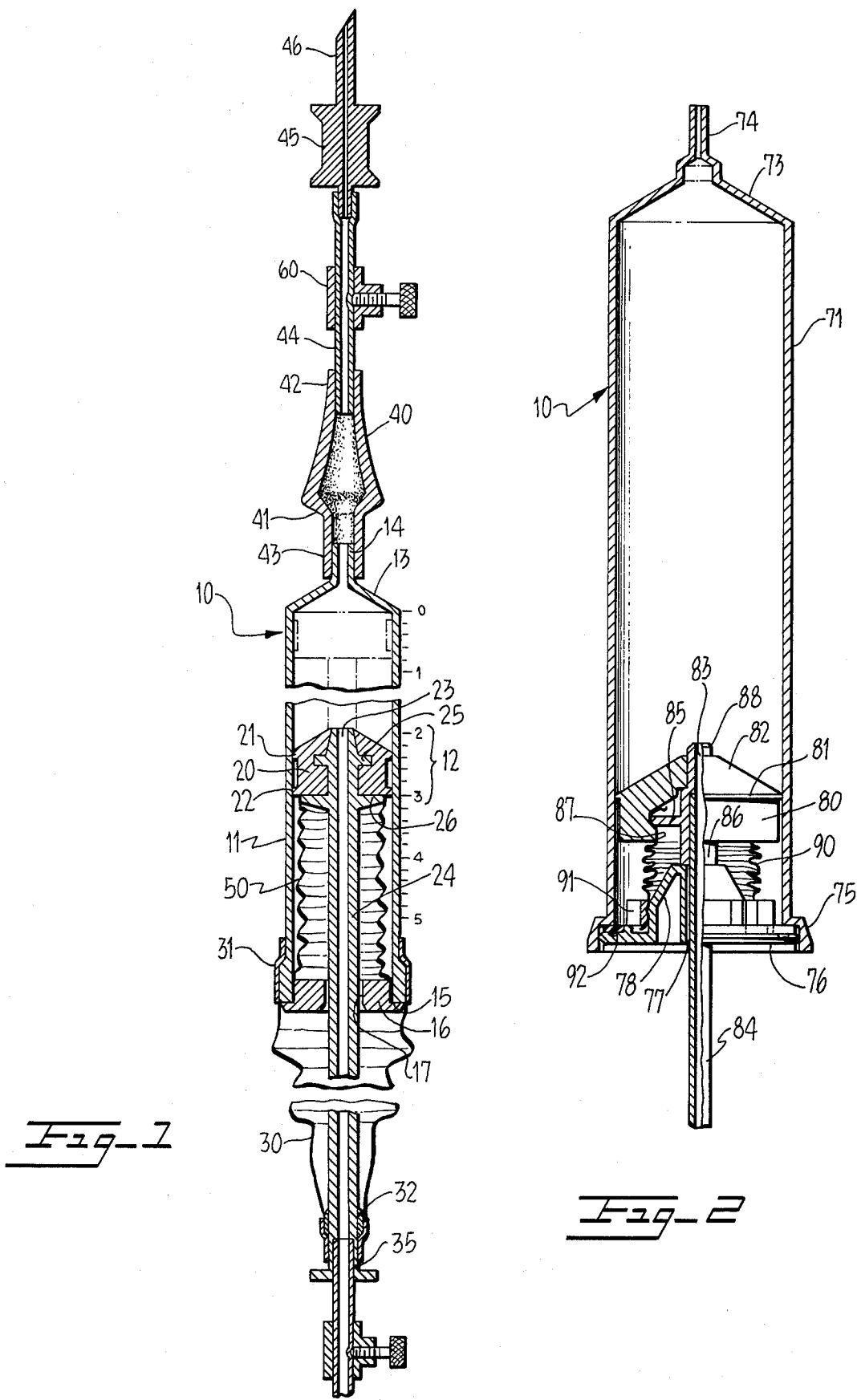

MEASURED VOLUME DRUG ADMINISTRATION DEVICE FOR USE WITH INTRAVENOUS FEEDING PUMP

BACKGROUND OF THE INVENTION

In recent years there has been great effort extended by researchers in the medical field for developing an intravenous feeding pump adapted to accurately measure and positively pump parenteral solution from a supply container into the veins of a patient without having to rely upon the force of gravity alone. Such pumps have many advantages in administering the parenteral fluid and many designs have been suggested, including two covered by patent applications of this applicant, namely, Ser. No. 431,753, filed Jan. 8, 1974 now U.S. Pat. No. 3,874,826 and Ser. No. 488,580, filed July 15, 1974.

Doctors often desire to introduce drugs into the blood stream of a patient, and whenever the patient is being fed intravenously, it is usually desirable to introduce the drug through the intravenous feeding system, as by injecting into the delivery tube to the patient. Quite often the drug is of such a character that it is advisable to dilute the drug in some predetermined ratio with the volume of solution being fed to the patient. The present device is directed to that end and provides a means whereby a desired volume of drug can first be diluted in a variable volume of the parenteral solution and then fed to the patient. Then, as soon as the drug has been administered, it is usually desirable to return to the feeding of the parenteral solution. The necessary changes, of course, must be done with a minimum chance of contamination of the drug or the solution from contact with the air during the various steps of the process, and great care must be taken to prevent the feeding of air into the blood stream of the patient. The device of the present invention provides a "closed system", i.e., one in which there is no possibility of contact of outside air with the fluid. The device is one that gives an accurate reading of volume at all times.

The device of the present invention is adapted to mix a drug injection with a predetermined amount of parenteral solution, in a variable ratio, to feed the same into the blood stream of the patient and then to return to the feed of the parenteral solution without breaking the connection between the supply container of parenteral fluid and the needle which is inserted into the blood vessel of the patient. It is particularly adapted to be used in cooperation with an intravenous feeding pump, such as the ones suggested by the applicant's aforementioned patent applications, or any of the other intravenous feeding pumps which have been designed for this purpose. It is also particularly adapted to be used in such a pump utilizing the alarm system described in the applicant's pending application, Ser. No. 488,581, filed July 15, 1974, which automatically sets off an alarm signal when the supply of parenteral fluid from the pump is either closed for any reason, or the volume pumped falls below the preset quantity to be delivered.

OBJECTS

It is an object of the present invention to provide a device for mixing a measured quantity of drug to be administered intravenously with a measured amount of parenteral fluid for injection into a patient.

It is another object of the invention to provide a drug mixing device for an intravenous feeding system that provides an accurate reading of volumes during the feeding of the same, as well as at the initial mixing thereof.

It is another object of the invention to provide a drug mixing device cooperating with an intravenous delivery pump adapted to mix a measured volume of drug and a measured volume of parenteral fluid for intravenous feeding into a patient in a conduit from which extraneous air is excluded at all times.

It is another object of the invention to provide a device for mixing a measured volume of drug and a measured volume of intravenous feeding fluid for administration to a patient which avoids all possibility of contamination from air and which does not require any change of the intravenous feeding needle or any part of the supply system after the drug has been administered.

These and further objects of the invention will be apparent from a disclosure which follows taken in conjunction with the drawing in which:

DRAWINGS

FIG. 1 is a cross-sectional view on an enlarged scale of the preferred device of the present invention; and FIG. 2 is a second embodiment of the device of the present invention, likewise being a cross-sectional view on an enlarged scale of the device.

The mixing device 10 (see FIG. 1) includes a cylindrical chamber 11 of a size somewhat larger than the conventional intravenous injection syringe commonly used in the medical profession. For example, in the form shown in FIG. 1 the cylinder 11 could have a volume of about 120 cc. (exclusive of the volume of the piston 20 to be described hereinafter) as contrasted with the usual medical syringe which has a volume of 5 cc. to 25 cc.

The cylinder preferably is marked with a series of indicia 12 indicating the various volumes that would be adapted for use in the particular device. Preferably, the upper end of the cylinder 11 is conically shaped to lead to a nipple 14 adapted to be inserted into the drug injection section 40 to be described hereinafter. The lower end of the cylinder 11 is provided with a completely open end 15 which is adapted to be closed by a cork member 16 provided with an enlarged central bore 17. It will be understood that in order to provide for movement of the piston 20 within the chamber formed by the cylinder 11, it is necessary that air can pass into or out of the area below the piston 20, to be described hereafter, so that the aperture 17 is somewhat larger than the hollow and rigid pin 24 to be described shortly.

A piston 20 is preferably provided with a pair of sealing rings 21, 22 (as shown in FIG. 1) which closely engage the walls of the cylinder 11. Preferably, the piston 20 is formed of a relatively soft and resilient material, such as rubber, or flexible plastic of medical grade. It is desired that no leakage be permitted around the sealing rings 21, 22 but that the piston 20 be sufficiently rigid to be readily moved within the piston chamber 11. The piston 20 is provided with an axial, or central, bore 23 into which is inserted a hollow rigid stem 24 which serves to deliver fluid to be pumped from the supply inlet 14 to a pump, such as disclosed in my applications above mentioned. Delivery tube 24 should be of rigid material, such as rigid plastic or glass, and is rigidly secured to the piston 20 by any suitable means, such as a flange 25 shown in FIG. 1, buried in the interior of the piston 20, and a seating bracket 26 engaging the lower face of the piston. Preferably, the upper end of the piston 20 is shaped to fit snugly against the upper end 13 of the cylindrical tube 11 so that when the piston is in its uppermost position there will be no empty space between the piston and the upper end 13 of the tube 11, in which situation fluid passing through the device will enter through the nipple 14 and pass directly into the interior bore 23 which will be in registration with the lower end of nipple 14. The hollow tube 24 should be of a length to extend beyond the end of the cylinder 11 so that it can be used to pull the piston 20 downwardly in the cylinder 11 when desired.

It is necessary to prevent contamination of the interior walls of the cylinder 11 below the piston 10 at all times. For this purpose I prefer to use a flexible, accordion pleated diaphragm 30 of somewhat conical shape, the upper end of which is sealed to the outside of the cylinder 11 by any suitable means, such as sealing ring 31, and the lower end of which is affixed to the lower end of the delivery tube 24 by any suitable means, such as the cemented gasket 32 which cements this end of the diaphragm to the tube 24. A flexible tube 35 leads from the lower end of the tube 24 to a suitable intravenous feeding pump, not shown herein. This tube 35 can be of conventional size if desired, as such tubes are somewhat flexible and can be stretched to fit over a registering member (such as tube 24) of somewhat similar size.

A somewhat pear-shaped drug injection chamber 40 has a lower shoulder 41, an upper end 42 adapted to receive the end of a conventional intravenous feeding tube 44 and the lower end 43 of which is adapted to be inserted over the nipple 14 leading into the mixing chamber 10. This drug injection chamber 40 is formed of suitable self-sealing rubber-like material of medical grade, so that the needle of a drug injection syringe can be inserted through the wall thereof, preferably through the shoulder section 41, to introduce the drug into the interior of the chamber 40, and when the syringe needle is withdrawn, will be self-sealing to prevent leakage of the material from the chamber or to prevent the leakage of air into the chamber. A short section of intravenous feeding tube 44 leads from the chamber 40 to a conventional bottle spike 45 which is provided with a hollow needle-like member 46 for penetrating the rubber seal of a bottle or bag of parenteral fluid.

It is assumed that the mechanism herein described will be assembled at the factory and will be sterilized and sealed in a sterile container so that it will be delivered where needed in a sterile condition, as would be the delivery pump with which the device is adapted to be associated. Obviously the device of the present invention should be delivered in a sterile condition to the patient. At that point, the needle 46 of the bottle spike is inserted through the cork of the bottle of fluid and the delivery tube 35 is immediately connected to the pump. The operator would then fill the system, including the device of the present invention, the pump and the delivery tube and needle with fluid to be delivered to the patient as would be governed by the directions for filling the pump. It is assumed that at this time the piston 20 is at its uppermost limit in the cylindrical tube 11. A tube clamp 60 is then applied to the tube 44 above the mixing device and clamped shut. A similar clamp is placed over the tube 35 and also closed shut. By this means the fluid in the system between the two clamps is sealed at both ends. The delivery tubes 44 and 35 will be completely filled with fluid, as well as the injection chamber 40. However, if the piston 20 is in the assumed position at the upper end of the chamber formed by the cylinder 11, there will be no fluid in the chamber except that contained within the hollow tube 24. At this point the doctor or nurse will stick a hypodermic needle filled with the proper amount of drug through the wall 41 of the chamber 40 and force the drug into that chamber. Since the fluid is incompressible, this introduction of a measured quantity of drug will force the piston 20 slightly downward. For example, if two cubic centimeters of drug were used, it would force the upper edge of the piston down below the mark below the zero shown in FIG. 1. At this point the upper clamp 60 is released and the rigid tube 24 is pulled down the proper amount to mix the drug with the designated amount of parenteral fluid — in the present instance, 22 cubic centimeters of parenteral fluid. At this point the upper tube clamp is again closed, so that no fluid can pass from the container of fluid (not shown) through the needle 46 of the bottle spike 45. The lower clamp 60 is then opened and the pump is started and will continue to pump fluid from the chamber within the cylinder 11 and above the piston 20 until that fluid is exhausted. With such pumping, air pressure will force the piston upwardly until it again comes to rest against the upper conical face 13 of the cylinder 11. It is believed obvious that the volume of fluid used by the pump is compensated for by the automatic movement of the piston and no air is needed to enable the pump to operate. The system is thus "closed" to the contamination of air at all times — even if the device is filled and emptied many times. If the pump (not shown) is provided with an alarm system, such as disclosed in my copending application, Ser. No. 488,581, filed July 15, 1974, an alarm will then be sounded, or a signal light energized, or the pump motor stopped, as is desired by the operator of the device. In any event, the nurse in charge of the patient will be notified that the drug has been completely administered and can immediately remove the upper clamp 60 and reinstitute pump operation. Since there has been no break in the system, there can be no contamination of the fluid delivered to the patient, nor any air introduced into the device, except that which is permitted to enter a bottle of fluid (not shown) in past practice. If the newer concept of delivering the feeding solution (parenteral fluid) in a flexible plastic bag is used there will be no air in the system at all. It will thus be seen that a predetermined volume of drug has been introduced into a desired volume of parenteral fluid, the mixture then pumped into the veins of a patient, and the patient returned to the positive feeding of the parenteral fluid — all without breaking the connection from the container of parenteral fluid to the pump or any contamination of the fluid or mixture resulting from a breaking of any part of the connection. It is important that after the administration of the drug mixture that means be provided to continue the administration of the base solution while maintaining safe and sterile conditions with the assurance that no air can enter the system.

It is believed it will be understood that the assembly herein described will supplant the usual drip chamber which is used in connection with bottles or bags of intravenous feeding fluid.

FIG. 1 shows a second form of germ barrier, or shield. This comprises an accordion pleated cylindrical membrane 50, the upper end of which is sealed between the base bracket 26 and the lower face of the piston 20 and the lower end of which is sealed between the interior wall of the cylinder 11 and the outer wall of the cork 16, as shown in FIG. 1. In this form, air can pass through the aperture 17 but cannot contaminate the interior wall of the chamber 11 as it is prevented in so doing by the seal 50. It will be understood that air must be free to pass from within or to within the lower part of the chamber formed by the cylinder 11 and piston 20 in order to permit movement of the piston 20; but as mentioned before, it is necessary to provide a germ barrier or shield between that air and the wall of the cylinder 11. In the first form, the air would be contained in the lower part of the chamber below the seal and within the outer diaphragm 30 (and there would be no inner sealing membrane 50). Since this is all sterilized at the time of assembly and sealed in a sterile container, this air would be sterile and could not contaminate the walls of the chamber. In the second form, the outer sealing membrane 50 is eliminated and the air from the outside can readily pass into the space within the inner membrane 50, thereby enabling the free movement of the piston 20 but preventing contamination of the inner walls of the cylinder 11.

The embodiment shown in FIG. 2 is quite similar to that shown in FIG. 1 in most respects. It comprises a cylindrical tube 71, the upper end of which is preferably conical shaped, as at 73, merging into a nipple 74 adapted to be inserted in the lower end, or outlet, 43 of a drug injection chamber 40, such as shown in FIG. 1 but not shown in connection with FIG. 2. The lower end of this embodiment is slightly enlarged, as at 75, to receive a cork or plug 76. In this form the cork 76 is provided with an inner wall 78 which is adapted to both strengthen the plug and to provide a guide wall for the rigid tube 84. As in the form shown in FIG. 1, there is an interior air passageway 77, so that air may pass from the exterior of the device into the chamber which is formed by the piston 80 and a flexible accordion pleated diaphragm 90.

A piston 80 is contained within the chamber formed by the cylinder 71. Preferably the piston has a conical upper end 82 shaped to fit the conical shaped end 73 of the tube 71 so that there will be no space between the two when the piston is in its uppermost position. The piston is provided with a sealing ring 81. In this embodiment, the piston is formed as an annular outer section 80 and an interior insert 86, which insert 86 has a bracket 85 that engages the inner wall of the piston 80. Since the piston is formed of resilient rubber-like material, it can be shaped to provide a bead 87 smaller in diameter than the bracket 85, whereby the bracket 85 can be inserted past the bead and thus firmly seated inside the piston 80. The aperture 83 in the upper end of this insert 86 provides a passageway from the inlet nipple 74 into a rigid tube 84 which leads to the outlet end of the device, thence into the inlet tube 35 of the pump.

An interior diaphragm 90, preferably accordion pleated as shown in FIG. 2, is seated between the piston 80 and the plug 76 as by means of clamping it between the interior wall of the piston 80 and the bracket 85 at its upper end, as shown; and at its lower end by a clamping ring 91 which surrounds the central wall 78 of the plug 76. In this form, which differs from that shown in FIG. 1 in this one important respect, a sterile filter air seal 92 is inserted in the plug 76, so that air may enter the chamber formed by the inner walls of the cylinder 71, the piston, the plug and the diaphragm 90. However, if this plug is of a type known to the medical profession which prevents the passage of bacteria, although air can do so, sterile conditions are maintained. The admission of air makes sterilization by gas and operation of the piston 80 easier than it otherwise would be and the filtering by the fine pore filter media mentioned prevents the entrance of bacteria. Except for this change, the form shown in FIG. 2 is essentially the same as that shown in FIG. 1 and it will be associated with the extraneous devices shown above the cylinder 11 in FIG. 1 and operation will be the same.

It is believed obvious that many modifications can be made in the device of the present invention without departing from the scope of its teachings. Accordingly, the appended claims should be given a construction not limited to the specific form disclosed herein.

I claim:

1. A drug measuring and mixing device adapted to be inserted in the flow system from a container of parenteral fluid to an intravenous feeding pump, which device comprises:
   a. A cylindrical container having an inlet and an outlet end;
   b. a piston within said cylindrical container;
   c. a stem secured to said piston and extending out of said cylindrical container;
   d. said piston and said stem being formed with a passageway extending through said piston and said stem and leading to a point beyond the outlet end of said cylindrical chamber;
   e. and a cylindrical flexible member secured between the piston and one end of the cylindrical container and serving to enclose the stem to provide a germ barrier preventing access of contaminated air to the interior wall of said cylindrical container between the piston and the outlet end of the cylindrical container;

2. The apparatus of claim 1 together with means for enabling the injection of a drug into said cylindrical container including a self-sealing section of fluid conduit affixed to the inlet end of said cylindrical container.

3. A drug measuring and mixing device adapted to be inserted in the flow system from a container of parenteral fluid to an intravenous feeding pump, which device comprises:
   a. a cylinder having an inlet in one end and an outlet in the other;
   b. a piston within said cylinder;
   c. a rigid tube extending through said piston and leading to a point without the outlet end of said cylinder;
   d. a germ barrier disposed within the cylinder preventing access of contaminated air to the interior wall of said cylinder between the piston and the outlet end of said container; and
   e. a drug injection section mounted on the inlet end of said cylinder, said section being adapted to engage the inlet end of said cylinder and to receive parenteral fluid from a supply of said fluid, said section being formed of a self-sealing rubber-like material permitting the insertion of the needle of a drug-injecting syringe therethrough and immediately sealing the aperture formed by such penetration upon removal of said needle.

4. The apparatus of claim 3 wherein the germ barrier comprises a flexible diaphragm.

5. The apparatus of claim 3 wherein the germ barrier comprises an air-proof diaphragm extending from the outlet end of said cylinder to the said piston and of a size to permit free movement of said piston within said cylinder.

6. The apparatus of claim 3 wherein the germ barrier comprises an air filter which permits the passage of air from the outside of the device into the chamber formed by the diaphragm and the inner wall of said cylinder but prevents the passage of bacteria therethrough.

* * * * *